United States Patent
Cohen

(10) Patent No.: US 12,350,258 B2
(45) Date of Patent: Jul. 8, 2025

(54) COMPOSITIONS AND METHODS FOR TREATMENT OF SKIN-RELATED DISEASES AND PROMOTING DERMATOLOGICAL HEALTH

(71) Applicant: Suzy Cohen, Broomfield, CO (US)

(72) Inventor: Suzy Cohen, Broomfield, CO (US)

(73) Assignee: Script Essentials, LLC, Superior, CO (US)

( * ) Notice: Subject to any disclaimer, the term of this patent is extended or adjusted under 35 U.S.C. 154(b) by 0 days.

(21) Appl. No.: 18/217,743

(22) Filed: Jul. 3, 2023

(65) Prior Publication Data

US 2023/0346751 A1    Nov. 2, 2023

Related U.S. Application Data

(63) Continuation of application No. 17/499,565, filed on Oct. 12, 2021, now abandoned.

(60) Provisional application No. 63/089,845, filed on Oct. 9, 2020.

(51) Int. Cl.
| | |
|---|---|
| *A61K 31/4188* | (2006.01) |
| *A61K 31/375* | (2006.01) |
| *A61K 33/30* | (2006.01) |
| *A61K 35/747* | (2015.01) |
| *A61K 36/87* | (2006.01) |
| *A61K 38/44* | (2006.01) |
| *A61K 47/44* | (2017.01) |

(52) U.S. Cl.
CPC ........ *A61K 31/4188* (2013.01); *A61K 31/375* (2013.01); *A61K 33/30* (2013.01); *A61K 35/747* (2013.01); *A61K 36/87* (2013.01); *A61K 38/446* (2013.01); *A61K 47/44* (2013.01)

(58) Field of Classification Search
CPC .... A61K 31/375; A61K 33/30; A61K 35/747; A61K 38/446; A61K 31/4188; A61K 36/87; A61K 47/44; A23L 33/135; A23L 33/10; A23L 33/105; A23L 33/15; A23L 33/16; A61P 17/00; C12Y 115/00
See application file for complete search history.

(56) References Cited

U.S. PATENT DOCUMENTS

2020/0199692 A1 *    6/2020   Mogna .................... C12N 1/20

FOREIGN PATENT DOCUMENTS

| WO | WO-2010013179 A1 * | 2/2010 | ........... A61K 8/9728 |
| WO | WO-2016149687 A1 * | 9/2016 | ......... A61K 31/4172 |

OTHER PUBLICATIONS

Dumoulin et al. (Clinical effects of an oral supplement rich in antioxidants on skin radiance in women. Clin Cosmet Investig Dermatol. Oct. 18, 2016;9:315-324. doi: 10.2147/CCID.S118920. PMID: 27799805; PMCID: PMC5076548.) (Year: 2016).*
Hintz et al (The Use of Plant Antimicrobial Compounds for Food Preservation, BioMed Research International, 2015, 246264. https://doi.org/10.1155/2015/246264) (Year: 2015).*
Katta et al (Diet and dermatology: the role of dietary intervention in skin disease. J Clin Aesthet Dermatol. Jul. 2014;7(7):46-51) (Year: 2014).*
Calatici et al (Perceived Age and Life Style. The Specific Contributions of Seven Factors Involved in Health and Beauty. Maedica (Bucur). Sep. 2017;12(3):191-201) (Year: 2017).*
Hannuksela et al (Hypersensitivity reactions to food additives. Allergy, 1987, 42: 561-575) (Year: 1987).*
Vollmer et al. (Enhancing Skin Health: By Oral Administration of Natural Compounds and Minerals with Implications to the Dermal Microbiome Int. J. Mol. Sci. 2018, 19, 3059) (Year: 2018).*
Weseler (Masquelier's grape seed extract: from basic flavonoid research to a well-characterized food supplement with health benefits. Nutr J 16, 5 (2017) (Year: 2017).*
Pullar et al., (The Roles of Vitamin C in Skin Health, Nutrients, 2017, 9, 866) (Year: 2017).*

* cited by examiner

*Primary Examiner* — Kade Ariani
(74) *Attorney, Agent, or Firm* — FisherBroyles LLP; Ian R. Walsworth

(57) ABSTRACT

The present disclosure relates to dietary supplements, for improving dermatological health. In embodiments, the composition is comprised of D-Biotin, grape seed extract, superoxide dismutase, zinc, Vitamin C, *Lactobacillus plantarum, Lactobacillus reuteri, Lactobacillus rhamnosus*, or combinations/sub-combinations thereof.

11 Claims, No Drawings

COMPOSITIONS AND METHODS FOR TREATMENT OF SKIN-RELATED DISEASES AND PROMOTING DERMATOLOGICAL HEALTH

CROSS-REFERENCE TO RELATED APPLICATIONS

The present application is a continuation of U.S. application Ser. No. 17/499,565, filed on Oct. 12, 2021, which in turn claims priority and the benefit under 35 U.S.C. § 119(e) to U.S. Provisional Patent Application Ser. No. 63/089,845 filed on Oct. 9, 2020. Each of the above-referenced applications is incorporated herein by reference in its entirety.

FIELD OF THE INVENTION

The present invention is directed to compounds for improving dermatological health. The present invention is also directed to methods for treatment of a disease or condition affecting the skin, as well as methods for formulating and administering a composition to address the same.

BACKGROUND OF THE INVENTION

The number of individuals suffering from or actively receiving treatment for skin-related disease has grown tremendously in the past 10 years. For example, recent studies have shown that approximately 85 million Americans are seen by a physician each year for treatment of skin disease. The estimated health care cost resulting from the same exceeds $75 billion. Presently, there are no fewer than 24 categories of skin disease recognized by the American Academy of Dermatology, including but not limited to acne, eczema, psoriasis, rosacea, ichthyosis, vitiligo, hives and dermatitis. With increasing cases of skin cancer and an aging population, the mortality rate is approximately 50%.

Accordingly, there is a long-felt but unresolved need to provide methods of treatment to address these and other problems related to skin-disease, which are the subject of the present disclosure.

SUMMARY OF THE INVENTION

The invention in embodiments relates to a compound, particularly in the form of a dietary supplement, which addresses skin-related disease and overcomes the shortcomings in the art with respect to improved skin health. As disclosed in more detail in the Detailed Description, the present invention provides compositions and methods for treating a person with unhealthy or diseased skin. Methods for forming the compound described herein are also disclosed.

Through experimentation it has been found that including various nutrients can be beneficial to people who have unhealthy skin or adverse dermatological conditions. In embodiments, a unique combination of the composition described herein is preferably administered orally in the form of a capsule, tablet, powder or lozenge. The unique combination has synergistic advantages over previously known compositions, all proportioned to provide the most benefit to people affected by the problems described above.

The composition is preferably comprised of a unique and novel formulation in pre-determined amounts, and further provides benefits previously unexpected. In a preferred embodiment, the composition is comprised of D-Biotin, grape seed extract (Preferably French grape seed extract), superoxide dismutase (preferably from melon), zinc, Vitamin C, *Lactobacillus plantarum*, *Lactobacillus reuteri*, *Lactobacillus rhamnosus*, or combinations/sub-combinations thereof.

In another preferred embodiment, the composition comprises the following, with variability in dosages listed below:
1) D-Biotin—between about 1,000 mcg and about 3,000 mcg;
2) A proprietary blend—between about 50 mg and about 300 mg—of the following:
   a) grape seed extract (preferably French grape seed extract);
   b) superoxide dismutase (preferably derived from melon);
   c) Zinc; and
   d) Vitamin C;
3) A proprietary blend—between about 1 Billion CFU/g and about 5 Billion CFU/g—of the following:
   a) *Lactobacillus plantarum*;
   b) *Lactobacillus reuteri*; and
   c) *Lactobacillus rhamnosus*;

In a most preferred embodiment, the composition comprises the following with dosages listed below:
1) D-Biotin—about 2,000 mcg;
2) A proprietary blend—about 150 mg—of the following:
   a) grape seed extract (preferably French grape seed extract);
   b) superoxide dismutase (preferably derived from melon);
   c) Zinc; and
   d) Vitamin C;
3) A proprietary blend—about 3 Billion CFU/g—of the following:
   a) *Lactobacillus plantarum*;
   b) *Lactobacillus reuteri*; and
   c) *Lactobacillus rhamnosus*

In one embodiment, the composition is provided as a dietary supplement. In one embodiment, the composition is administered in the form of a vegetable-based capsule, and two capsules are administered daily. In another embodiment, the composition is administered in the form of a powder, a gummy chew, a tablet, a lozenge or a liquid extract. In a preferred embodiment, the formulation is unflavored, but in further embodiments, the composition may contain one or more palatability agents to favorably alter the taste of the composition for human consumption.

Methods for treatment of individuals with skin-related disease or impairment, including but not limited to any of the disorders listed above, are also an express part of this disclosure. Methods for formulating and administering the supplement described herein are also within the scope of the present disclosure.

It is to be expressly understood that the above-described embodiments, objectives, and configurations are neither complete nor exhaustive. The Summary of the Invention is neither intended, nor should it be construed as being representative of the full extent and scope of the present invention. Other advantages will be apparent from the disclosure of the invention(s) contained herein.

Embodiments of the present invention are set forth in various levels of detail in the Summary of the Invention, and no limitation as to the scope of the present invention is intended by either the inclusion or non-inclusion of elements in this Summary of the Invention. Additional aspects of the present invention will be readily apparent from the view of one of ordinary skill in the art.

DETAILED DESCRIPTION

Although the following text sets forth a Detailed Description of numerous different embodiments, it should be understood that the legal scope of the description is defined by the words of the claims set forth at the end of this disclosure. The Detailed Description is to be construed as exemplary only, and does not describe every possible embodiment since describing every possible embodiment would be impractical, if not impossible. Numerous alternative embodiments could be implemented, using either current technology or technology developed after the filing date of this patent, which would be encompassed by the scope of the claims.

As used herein, references to "the present invention" or aspects thereof should be understood to mean certain embodiments of the present invention and should not necessarily be construed as limiting all embodiments to a particular description.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, amounts, dimensions, conditions, and so forth used in the specification and claims are to be understood as being modified in all instances by the term "about".

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

In varying embodiments described herein, the present invention relates to a compound that improves an individual's skin and/or treats skin-related diseases. Certain elements of the novel compounds and methods for formulating the same are described in varying levels of detail herein.

Composition:

In embodiments, the composition is comprised of the foregoing elements:
1) D-Biotin;
2) A first proprietary blend comprising:
   a) grape seed extract (preferably French grape seed extract);
   b) superoxide dismutase (preferably derived from melon);
   c) Zinc; and
   d) Vitamin C;
3) A second proprietary blend comprising:
   a) *Lactobacillus plantarum*;
   b) *Lactobacillus reuteri*; and
   c) *Lactobacillus rhamnosus*

Certain of these components are described in greater detail below.

D-Biotin

D-biotin has an important role in overall health of an individual. D-Biotin been shown to help the body convert food into energy. In addition, it can boost hair and nails and helps manage blood sugar levels, among other benefits. D-Biotin has also been shown to have a positive impact if taken during pregnancy.

In a preferred embodiment, the compound is comprised of a pre-determined amount of D-Biotin. In a most preferred embodiment, the compound is comprised of about 2,000 mcg of D-Biotin.

Vitamin C

Vitamin C, also known as ascorbic acid, is a water-soluble vitamin. In a most preferred embodiment, the compound is comprised of a pre-determined amount of vitamin C.

Vitamin C is a cofactor in at least eight enzymatic reactions, which through experimentation have been found to support healthy skin and provide anti-aging properties. These enzymatic reactions are important, and increasing evidence indicates vitamin C improves the absorption of minerals, most notably iron, in adults and children.

Furthermore, vitamin C is essential to wound healing and in the creation of skin, tendons, ligaments, and blood vessels and other regions of the human anatomy.

In a preferred embodiment, the composition comprises a first proprietary blend that is comprised of Vitamin C.

Zinc

In a preferred embodiment, the composition comprises a first proprietary blend that is comprised of Zinc. In a preferred embodiment, the Zinc is provided as Zinc Glycinate.

Absent Elements

In addition, the composition of a preferred embodiment is substantially free of the following common allergens: gluten, wheat, eggs, peanuts, tree nuts, dairy, sugar and fish/shellfish. The composition preferably does not contain artificial colors, flavors, or preservatives, and is free from magnesium stearate (a common lubricant used in the manufacture of pharmaceuticals and dietary supplements).

Additional Elements

In varying embodiments, the composition can further comprise variances, particularly with respect to encapsulation and/or powder formulations. The composition may be provided in the form of a capsule, and may made with Hypromellose (HPMC), Nu-RICE® and/or Nu-FLOW® ingredients.

According to certain embodiments, the compositions described herein can further be provided with one or more palatability agents. These palatability agents serve to add flavor to the composition so that an effective dosage is easier to be ingested. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, yeast hydrolysates, and combinations thereof.

Methods

An aspect of the invention is a method to treat a patient experiencing skin disease, skin cancer, acne, eczema, psoriasis, rosacea, ichthyosis, vitiligo, hives, dermatitis, and seborrheic dermatitis, among other conditions, with a composition comprising a unique combination and blend of D-Biotin, grape seed extract (Preferably French grape seed extract), superoxide dismutase (preferably from melon), zinc, Vitamin C, *Lactobacillus plantarum, Lactobacillus reuteri, Lactobacillus rhamnosus*, or combinations/sub-combinations thereof.

According to one embodiment, during the method the patient is treated by providing an effective amount of the composition. In certain embodiments, the composition can be taken by the patient daily, with no regard to meals or time of day ingested. In one such embodiment, the composition is administered daily to a patient in need thereof in the form of two capsules that are fit for human consumption.

According to another embodiment, a method to prepare a compound is disclosed. The components are mixed in a proprietary blend and may be provided in a delivery device, for example, in the form of a capsule, tablet, lozenge or powder.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. Ranges have been discussed and used within the forgoing description. One of skill in the art will understand that any sub-range within the stated range would be suitable, as would any number within the broad range, without deviating from the spirit of the present invention.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment.

What is claimed is:

1. A method for treating a skin-related condition by administering an effective amount of a composition to a patient, wherein the composition comprises:
   2,000 mcg of D-Biotin;
   150 mg of a first blend, comprising:
      grape seed extract;
      superoxide dismutase;
      Zinc; and
      Vitamin C;
   3 Billion CFU/g of a second blend, comprising:
      *Lactobacillus plantarum;*
      *Lactobacillus reuteri;* and
      *Lactobacillus rhamnosus;*
   wherein the composition is devoid of other ingredients, components or additives selected from the group consisting of gluten, wheat, egg, peanuts, tree nuts, dairy, sugar, corn, soy, artificial colors, preservatives, fish and shellfish; and
   wherein the effective amount of the composition is administered to the patient one time each day.

2. The method of claim 1, wherein the composition is administered orally in the form of a capsule.

3. The method of claim 1, wherein the composition administered to the patient further comprises at least one palatability agent.

4. The method of claim 3, wherein the at least one palatability agent is selected from the group consisting of plant oils, plant hydrolysates, yeast, and yeast hydrolysates.

5. A method for treating a skin-related disease, comprising:
   administering an effective amount of a composition to a patient, wherein the composition consists of:
   2,000 mcg of D-Biotin;
   150 mg of a first blend consisting of:
      grape seed extract;
      superoxide dismutase;
      Zinc; and
      Vitamin C;
   3 Billion CFU/g of a second blend consisting of:
      *Lactobacillus plantarum;*
      *Lactobacillus reuteri;* and
      *Lactobacillus rhamnosus.*

6. The method of claim 5, wherein the composition is administered orally in the form of a capsule, tablet, lozenge or powder.

7. The method of claim 5, wherein the composition administered to the patient does not comprise additives selected from the group consisting of gluten, wheat, egg, peanuts, tree nuts, dairy, sugar, corn, soy, artificial colors, preservatives, fish and shellfish.

8. The method of claim 5, wherein the composition is administered orally to the patient between 3-4 times each day.

9. The method of claim 5, wherein the skin-related disease is selected from the group consisting of acne, ichthyosis, dermatitis, and seborrheic dermatitis.

10. The method of claim 5, wherein the composition is administered orally to the patient two times each day.

11. A method for treating ichthyosis, comprising:
    administering an effective amount of a composition to a patient, wherein the composition is administered twice each day and consists of:
    2,000 mcg of D-Biotin;
    150 mg of a first blend consisting of:
       grape seed extract;
       superoxide dismutase;
       Zinc; and
       Vitamin C;
    3 Billion CFU/g of a second blend consisting of:
       *Lactobacillus plantarum;*
       *Lactobacillus reuteri;* and
       *Lactobacillus rhamnosus;*
    wherein the superoxide dismutase in the first blend is derived exclusively from melon;
    wherein the composition administered to the patient further comprises at least one palatability agent selected from the group consisting of plant oils, plant hydrolysates, yeast, and yeast hydrolysates; and
    wherein the composition is devoid of additives selected from the group consisting of gluten, wheat, egg, peanuts, tree nuts, dairy, sugar, corn, soy, artificial colors, preservatives, fish and shellfish.

* * * * *